(12) United States Patent  (10) Patent No.: US 9,085,498 B2
Corradi et al.  (45) Date of Patent: Jul. 21, 2015

(54) COMBINED XYLENE ISOMERIZATION AND TRANSALKYLATION PROCESS UNIT

(71) Applicant: UOP LLC, Des Plaines, IL (US)

(72) Inventors: Jason T. Corradi, Arlington Heights, IL (US); David W. Ablin, Arlington Heights, IL (US); David W. Liu, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/279,879

(22) Filed: May 16, 2014

(65) Prior Publication Data

US 2014/0249341 A1  Sep. 4, 2014

Related U.S. Application Data

(62) Division of application No. 13/626,191, filed on Sep. 25, 2012, now Pat. No. 8,822,747.

(60) Provisional application No. 61/578,609, filed on Dec. 21, 2011.

(51) Int. Cl.
| | |
|---|---|
| C07C 6/12 | (2006.01) |
| C07C 15/08 | (2006.01) |
| C07C 6/06 | (2006.01) |
| B01D 3/14 | (2006.01) |
| C07C 5/27 | (2006.01) |

(52) U.S. Cl.
CPC . *C07C 6/06* (2013.01); *B01D 3/141* (2013.01); *C07C 5/2702* (2013.01); *C07C 5/2729* (2013.01)

(58) Field of Classification Search
USPC .................. 585/319, 470, 477, 478
See application file for complete search history.

(56) References Cited

U.S. PATENT DOCUMENTS

2009/0032386 A1* 2/2009 Negiz et al. .................. 202/158

* cited by examiner

*Primary Examiner* — Thuan D Dang

(57) ABSTRACT

The xylene isomerization process unit and the transalkylation process units are combined in the present invention. A fractionation column can be shared by the two units, reducing the capital cost of the complex. In some embodiments, a split shell fractionation column and a split separator can be used.

4 Claims, 4 Drawing Sheets

_US 9,085,498 B2_

COMBINED XYLENE ISOMERIZATION AND TRANSALKYLATION PROCESS UNIT

CROSS-REFERENCE TO RELATED APPLICATION

This application is a Division of prior copending U.S. application Ser. No. 13/626,191 which was filed Sep. 25, 2012, which is incorporated herein by reference in its entirety and which claims benefit of U.S. Provisional Application No. 61/578,609 which was filed on Dec. 21, 2011.

BACKGROUND OF THE INVENTION

A typical aromatics complex includes a xylene isomerization unit and a transalkylation unit. The xylene isomerization unit and the transalkylation unit are completely separate process units, each with its own separator, recycle gas compressor, and fractionation column.

An example of a current aromatics complex is shown in FIG. 1. The complex includes a xylene isomerization unit 5 and the transalkylation unit 10. The isomerization unit 5 has an isomerization reactor 15. The feed 20 is pre-heated in a heat exchanger 25 and further heated in a charge heater 30 before entering the isomerization reactor 15. The effluent 35 from the isomerization reactor 15 is sent to the heat exchanger 25, the condenser 37, and then to the separator 40. The overhead 45 from the separator 40 is sent to a recycle gas compressor 50 and is recycled back to the isomerization reactor 15. Make-up hydrogen 55 is added to the compressed overhead 45 as needed. The liquid 60 from the separator 40 is sent to a detoluene fractionation column 65. The overhead 70 is sent to the condenser 73, and the overhead receiver 75. The liquid 80 from the overhead receiver 75 is divided into a reflux stream 85 that is sent back to the detoluene fractionation column 65 and a net overhead stream 90 that is sent to a stripper column 95. The overhead 100 from the stripper column 95 is combined with the vapor 70 from the column 65 and recycled back to the condenser 73 and separator 75. Overhead vapor 105 is removed from overhead receiver 75 to maintain column pressure control. The bottoms 110 from the stripper column 95 is sent to a benzene column or to an aromatic extraction unit (not shown). The bottoms 115 from the detoluene fractionation column 65 is divided into stream 120, which is sent to the reboiler 125 and back to the detoluene fractionation column 65, and stream 130, which is sent to a xylene column (not shown).

The transalkylation unit 10 has a transalkylation reactor 135. The feed 140 is pre-heated in a heat exchanger 145 and further heated in a charge heater 150 before entering the transalkylation reactor 135. The effluent 155 from the transalkylation reactor 135 is sent to the heat exchanger 145, the condenser 157, and then to the separator 160. The overhead 165 from the separator 160 is sent to a recycle gas compressor 170 and is recycled back to the transalkylation reactor 135. Make-up hydrogen 175 is added to the compressed overhead 165 as needed. The liquid 180 from the separator 160 is sent to a detoluene fractionation column 185. The overhead 190 is sent to a condenser 193, and overhead receiver 195. The effluent 200 from the overhead receiver 195 is divided into a reflux stream 205 that is sent back to the detoluene fractionation column 185 and a net overhead stream 210 that is sent to a stripper column 215. The overhead 220 from the stripper column 215 is combined with the vapor 190 from the column 185 and recycled back to the condenser 193 and overhead receiver 195. Overhead vapor 220 is removed from overhead receiver 195 to maintain column pressure control. The bottoms 230 from the stripper column 215 is sent to a benzene column or to an aromatic extraction unit (not shown). The bottoms 235 from the detoluene fractionation column 185 is divided into stream 240, which is sent to the reboiler 245 and back to the detoluene fractionation column 185, and stream 250, which is sent to a xylene column (not shown).

The duplication of equipment, such as the separators, gas recycle compressors, and fractionation columns, to process streams containing similar components, although in different amounts, adds significant capital cost to the aromatics complex.

SUMMARY OF THE INVENTION

One aspect of the invention is a combined xylene isomerization and transalkylation process. In one embodiment, the process includes isomerizing a feed stream in an isomerization reactor in the presence of an isomerization catalyst under isomerization conditions to produce an isomerization product; transalkylating a feed stream in a transalkylation reactor in the presence of a transalkylating catalyst under transalkylating conditions to produce a transalkylation product; separating the isomerization product in an isomerization separator to produce an isomerization separator bottoms stream; separating the transalkylation product in a transalkylation separator to produce a transalkylation separator bottoms stream; providing a split shell fractionation column having a baffle separating the fractionation column into two sides, the fractionation column having an isomerization inlet on the isomerization side of the baffle and a transalkylation inlet on the transalkylation side of the baffle, the baffle extending from a bottom of the column to a location above a highest inlet; introducing the isomerization separator bottoms stream into the isomerization side of the fractionation column through the isomerization inlet; introducing the transalkylation separator bottoms stream into the transalkylation side of the fractionation column through the transalkylation inlet; fractionating the isomerization separator bottom stream in the isomerization side of the fractionation column to produce a fractionation column isomerization bottoms stream; and fractionating the transalkylation separator bottom stream in the transalkylation side of the fractionation column to produce a fractionation column transalkylation bottoms stream.

Another aspect of the invention is a combined xylene isomerization and transalkylation process unit. In one embodiment, the process unit includes an isomerization reactor; a transalkylation reactor; an isomerization separator in fluid communication with the isomerization reactor; a transalkylation separator in fluid communication with the transalkylation reactor; and a split shell fractionation column having a baffle separating the fractionation column into two sides, the fractionation column having an isomerization inlet on the isomerization side of the baffle and a transalkylation inlet on the transalkylation side of the baffle, the baffle extending from a bottom of the column to a location above a highest inlet; the isomerization inlet in fluid communication with a bottoms stream from the isomerization separator, and the transalkylation inlet in fluid communication with a bottoms stream from the transalkylation separator.

Another aspect of the invention is a split shell fractionation column. In one embodiment, the fractionation unit includes a split shell fractionation column having a baffle separating the column into two sides, the column having a first inlet on the first side of the baffle and a first bottoms outlet on the first side of the column, and a second inlet on the second side of the baffle, and a second bottoms outlet on the second side of the column, the baffle extending from a bottom of the column to a location above a highest inlet.

Another aspect of the invention is a split shell separator. In one embodiment, the split shell separator includes a single separator having a baffle extending from a bottom of the separator to a location above a liquid level in the separator, a first inlet on a first side of the baffle, and a first bottoms outlet on the first side of the baffle, and a second inlet on a second side of the baffle, and a second bottoms outlet on the second side of the baffle.

Another aspect of the invention is a combined xylene isomerization and transalkylation process. In one embodiment, the process includes isomerizing a feed stream in an isomerization reactor under isomerization conditions to produce an isomerization product; transalkylating a feed stream in a transalkylation reactor under transalkylating conditions to produce a transalkylation product; combining the isomerization product and the transalkylation product; introducing the combined product into a single separator; separating the combined product in the separator to produce a separator bottoms stream; and fractionating the separator bottoms stream in a fractionation column to produce a fractionation column bottoms stream.

BRIEF DESCRIPTION OF THE INVENTION

DETAILED DESCRIPTION OF THE INVENTION

The xylene isomerization process unit and the transalkylation process units are combined in the present invention. A single detoluene fractionation column can be shared by the two units. In some embodiments, the separator and recycle gas compressor can also be shared. The removal of one the fractionation columns, as well as one of the separators and one of the gas recycle compressors in some embodiments, significantly reduces the capital cost of the unit.

The development of new transalkylation catalysts, which allow the transalkylation reactor to operate at lower pressures, makes the sharing of equipment between the isomerization section and the transalkylation section practical.

Figure 1:
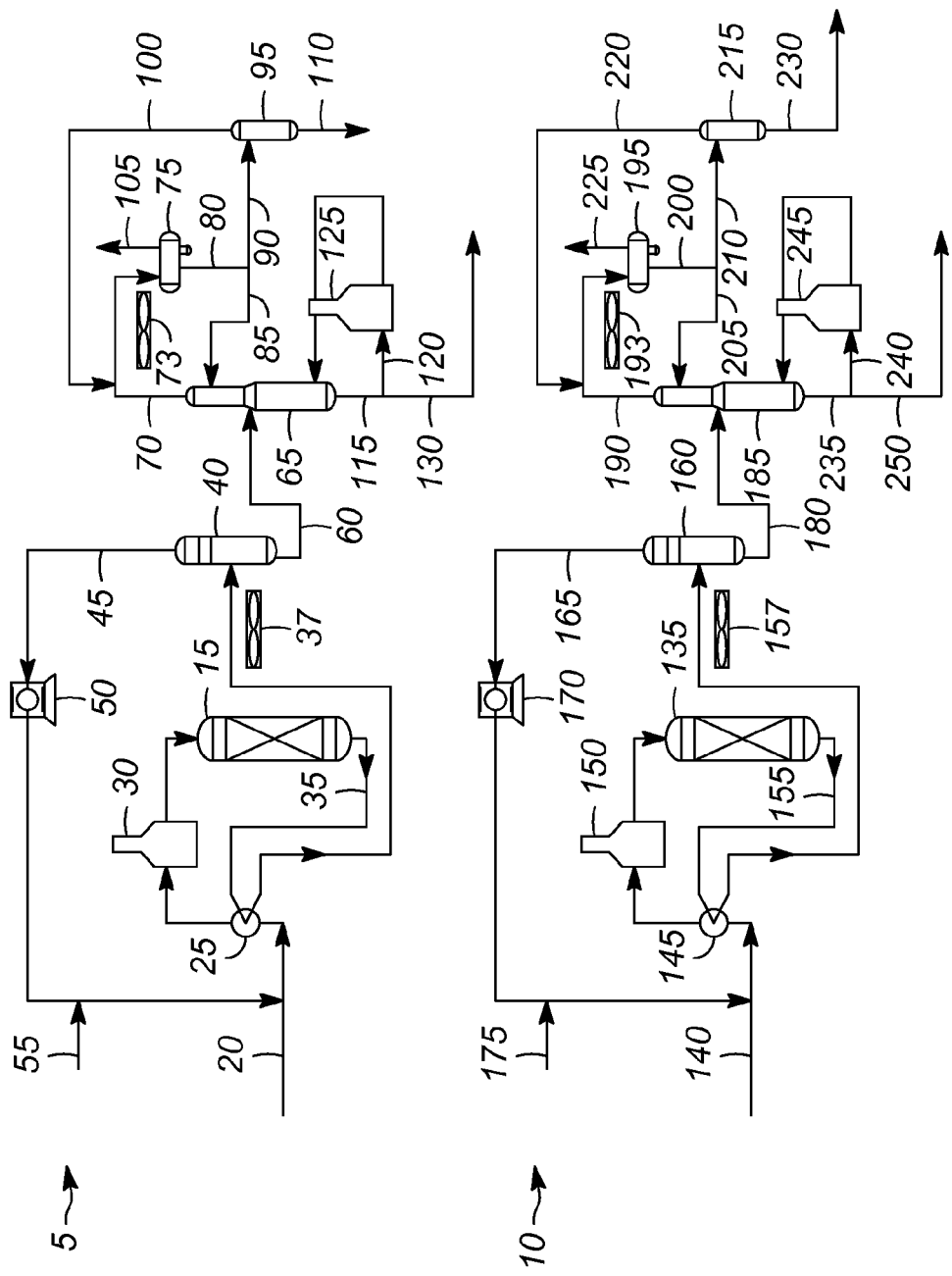
FIG. 1 is an illustration of a prior art complex having separate isomerization and transalkylation process units.
Figure 2:
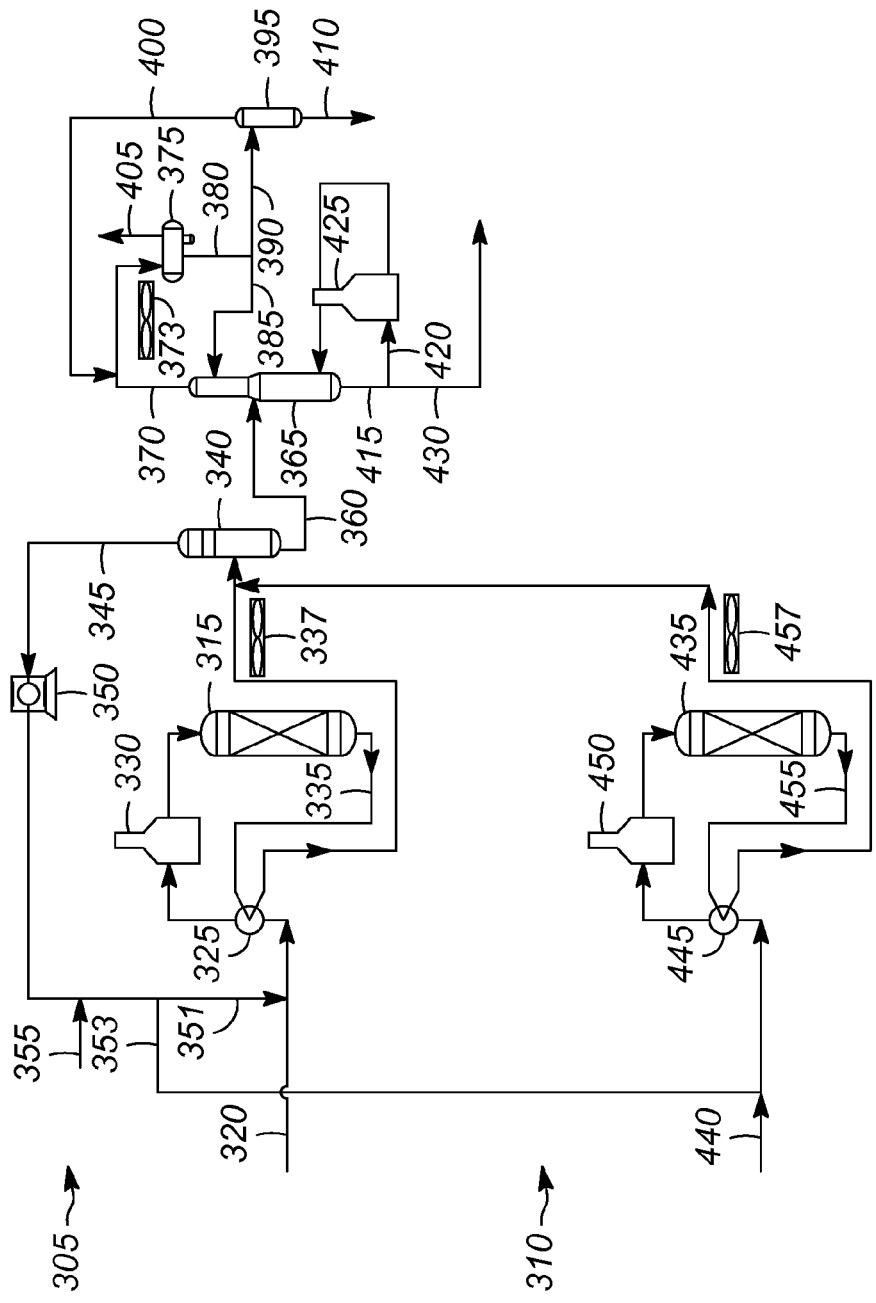
FIG. 2 is one embodiment of a combined isomerization and transalkylation process unit.

In one embodiment shown in FIG. 2, the isomerization and transalkylation reactor zones are independent, i.e., each has its own reactor feed heat exchanger, charge heater, reactor, and product condenser. The effluent from each reactor section is sent to a common separator.

The isomerization unit 305 has an isomerization reactor 315. The feed 320 is pre-heated in a heat exchanger 325 and further heated in a charge heater 330 before entering the isomerization reactor 315. The effluent 335 from the isomerization reactor 315 is sent to the heat exchanger 325, and the condenser 337.

The transalkylation unit 310 has a transalkylation reactor 435. The feed 440 is pre-heated in a heat exchanger 445 and further heated in a charge heater 450 before entering the transalkylation reactor 435. The effluent 455 from the transalkylation reactor 435 is sent to the heat exchanger 445, and the condenser 457.

The effluent 335 from the isomerization reactor 315 is combined with the effluent 455 from the transalkylation reactor 435 and sent to a common separator 340. The overhead 345 from the common separator 340 is sent to a recycle gas compressor 350. A portion 351 of the overhead is recycled back to the isomerization reactor 315, and a portion 353 is recycled back to the transalkylation reactor 435. The recycle can be split using flow controls valves. Make-up hydrogen 355 is added to the compressed overhead 345 as needed.

The liquid 360 from the separator 340 is sent to a common detoluene fractionation column 365. The overhead 370 is sent to the condenser 373, and the overhead receiver 375. The liquid 380 from the separator 375 is divided into a reflux stream 385 that is sent back to the detoluene fractionation column 365 and a net overhead stream 390 that is sent to a stripper column 395. The overhead 400 from the stripper column 495 is combined with the vapor 370 from the column 365 and recycled back to the condenser 373 and overhead receiver 375. Overhead vapor 405 is removed from overhead receiver 375 to maintain column pressure control. The bottoms 410 from the stripper column 395 is sent to a benzene column or to an aromatic extraction unit (not shown). The bottoms 415 from the detoluene fractionation column 365 is divided into stream 420, which is sent to the reboiler 425 and back to the detoluene fractionation column 365, and stream 430, which is sent to a xylene column (not shown).

This approach involves the maximum capital savings because it eliminates all of the potentially redundant equipment, i.e., separator, recycle gas compressor, and detoluene fractionation column and related equipment.

But the capital saving comes with a substantial energy penalty. The use of the common separator and fractionation column requires mixing the xylene stream from the isomerization reactor with the xylene stream from the transalkylation reactor into a single feed stream to the xylene column. However, those streams have significantly different amounts of A9+ components, with the isomerization stream having very little A9+, and the transalkylation stream having a substantial amount of A9+. Current systems keep the two streams separate and feed them to different tray locations in the downstream xylene column to reduce the reflux required to produce the feed for the xylene separation process and fuel firing by about 20 to 30%.

The energy problem can be solved by maintaining the separate liquid streams so that the isomerization stream with low levels of A9+ components, and the transalkylation stream with higher levels of A9+ components can be fed to the appropriate trays in the xylene column. In order to do that, a split-shell fractionation column has been developed which segregates the column bottoms product streams.

The split shell fractionation column includes a baffle which divides the tray section into two independent sides. The baffle extends to the bottom of the column, keeping the sump liquid separated. The baffle is solid and comprised of the same material as the fractionation column shell. The top of the baffle extends to a location above the highest feed tray. The highest feed tray is the highest feed tray for the isomerization side, the transalkylation side, or any other feed trays that might be present. It should extend to the level of about half of the trays above the highest feed inlet. This would generally be at least four trays above the highest feed tray, typically about five trays above it. Above means closer to the vapor outlet of the column (or other equipment), and below means closer to the liquid outlet.

The liquid streams from the isomerization and transalkylation separators are fed to opposite sides of the baffle. The baffle does not have to divide the column equally. One side can be larger than the other depending on the design of the particular complex and the size of the liquid streams from the isomerization reactor and the transalkylation reactor.

Figure 3:
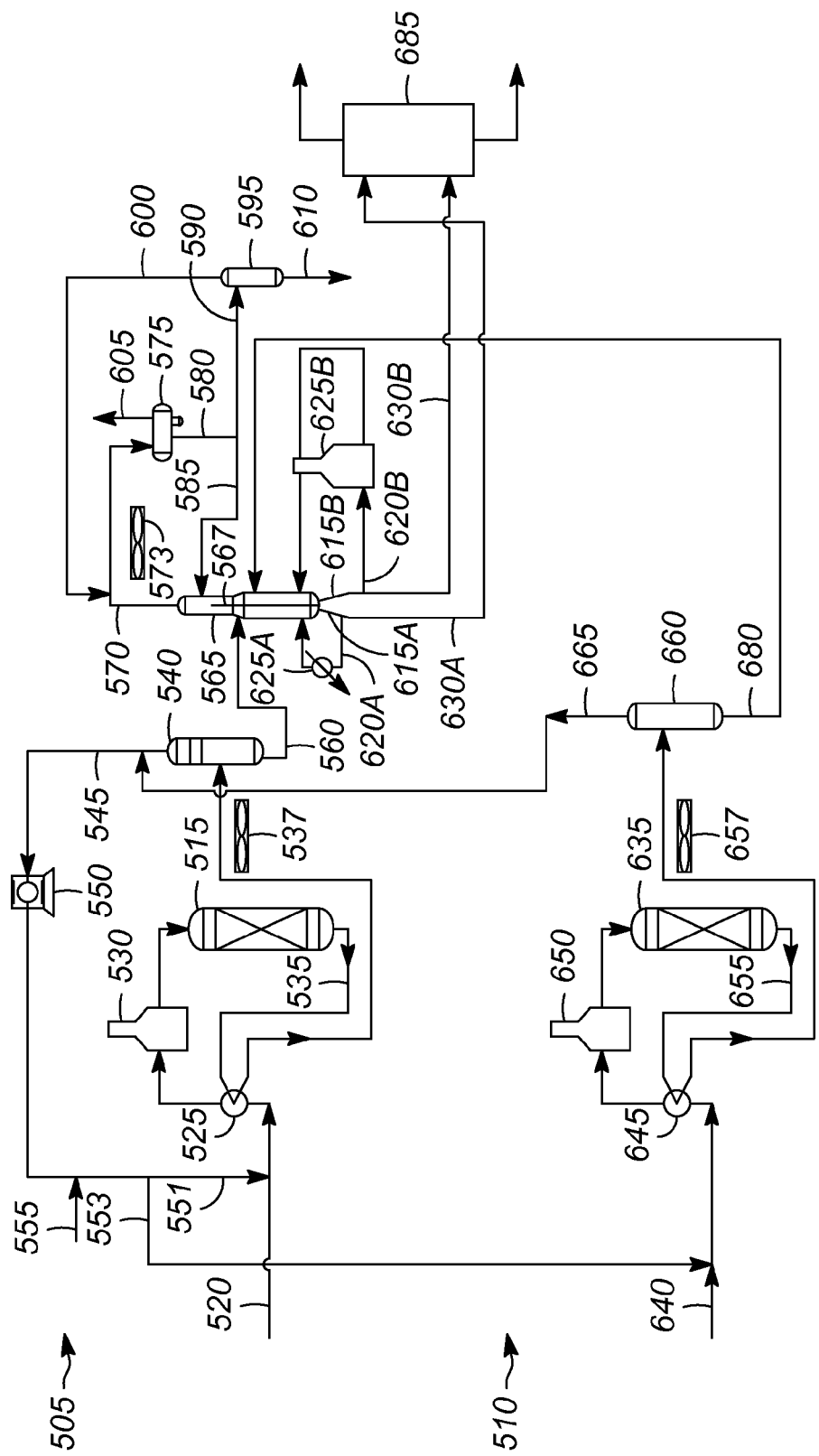
FIG. 3 is another embodiment of a combined isomerization and transalkylation process unit.

FIG. 3 illustrates one embodiment of a combined isomerization and transalkylation unit with a split shell fractionation column.

The isomerization unit 505 has an isomerization reactor 515. The feed 520 is pre-heated in a heat exchanger 525 and further heated in a charge heater 550 before entering the isomerization reactor 515. The effluent 535 from the isomerization reactor 515 is sent to the heat exchanger 525, the condenser 537, and the separator 540.

The overhead 545 from the separator 540 is sent to a recycle gas compressor 550. A portion 551 is recycled back to the isomerization reactor 515, and a portion 553 is recycled back to the transalkylation reactor 635. The recycle can be split using flow controls valves. Make-up hydrogen 555 can be added to the compressed overhead 545 if needed.

The transalkylation unit 510 has a transalkylation reactor 635. The feed 640 is pre-heated in a heat exchanger 645 and further heated in a charge heater 650 before entering the transalkylation reactor 635. The effluent 655 from the reactor 635 is sent to the heat exchanger 645, the condenser 657, and the separator 660.

The overhead 665 from the separator 640 is sent to recycle gas compressor 550.

The fractionation column 565 is a split shell fractionation column. It includes a baffle 567 extending from the bottom of the column dividing the tray section of the fractionation column into two sides. The liquid 560 from the separator 540 is sent to one side, and the liquid 680 from the separator 660 is sent to the other side. The baffle extends above the level of both feed inlets.

The overhead 570 is sent to the condenser 573, and the overhead receiver 575. The liquid 580 from the overhead receiver 575 is divided into a reflux stream 585 that is sent back to the split shell fractionation column 565 and a net overhead stream 590 that is sent to a stripper column 595. The overhead 600 from the stripper column 595 is combined with the vapor 570 from the overhead receiver 575 and recycled back to the condenser 573 and overhead receiver 575. Overhead vapor 600 is removed from overhead receiver 575 to maintain column pressure control. The bottoms 610 from the stripper column 595 is sent to a benzene column or to an aromatic extraction unit (not shown).

Because the baffle 567 extends to the bottom of the split shell fractionation column 565, the liquid bottoms from the isomerization side and the transalkylation side remain separated. The bottoms 615A from the isomerization side of the split shell fractionation column 565 is divided into stream 620A, which is sent to the reboiler 625A and back to the isomerization side of the split shell fractionation column 565, and stream 630A, which is sent to a xylene column 685. Stream 630A is the upper feed for the xylene column 685 because of its low A9+ content.

The bottoms 615B from the transalkylation side of the split shell fractionation column 565 is divided into stream 620B, which is sent to the reboiler 625B and back to the transalkylation side of the split shell fractionation column 565, and stream 630B, which is sent to the xylene column 685. Stream 630B is the lower feed for the xylene column 685 because of its higher A9+ content.

In another embodiment, there is a split separator in addition to the split shell fractionation column. This arrangement removes one of the separators. The split separator has a baffle extending from the bottom to a point near the top of the vessel and substantially above the normal level of the liquid. The separator does not have to be divided equally; one side can be larger than the other depending on the design of the complex and the size of the isomerization and transalkylation streams.

Figure 4:
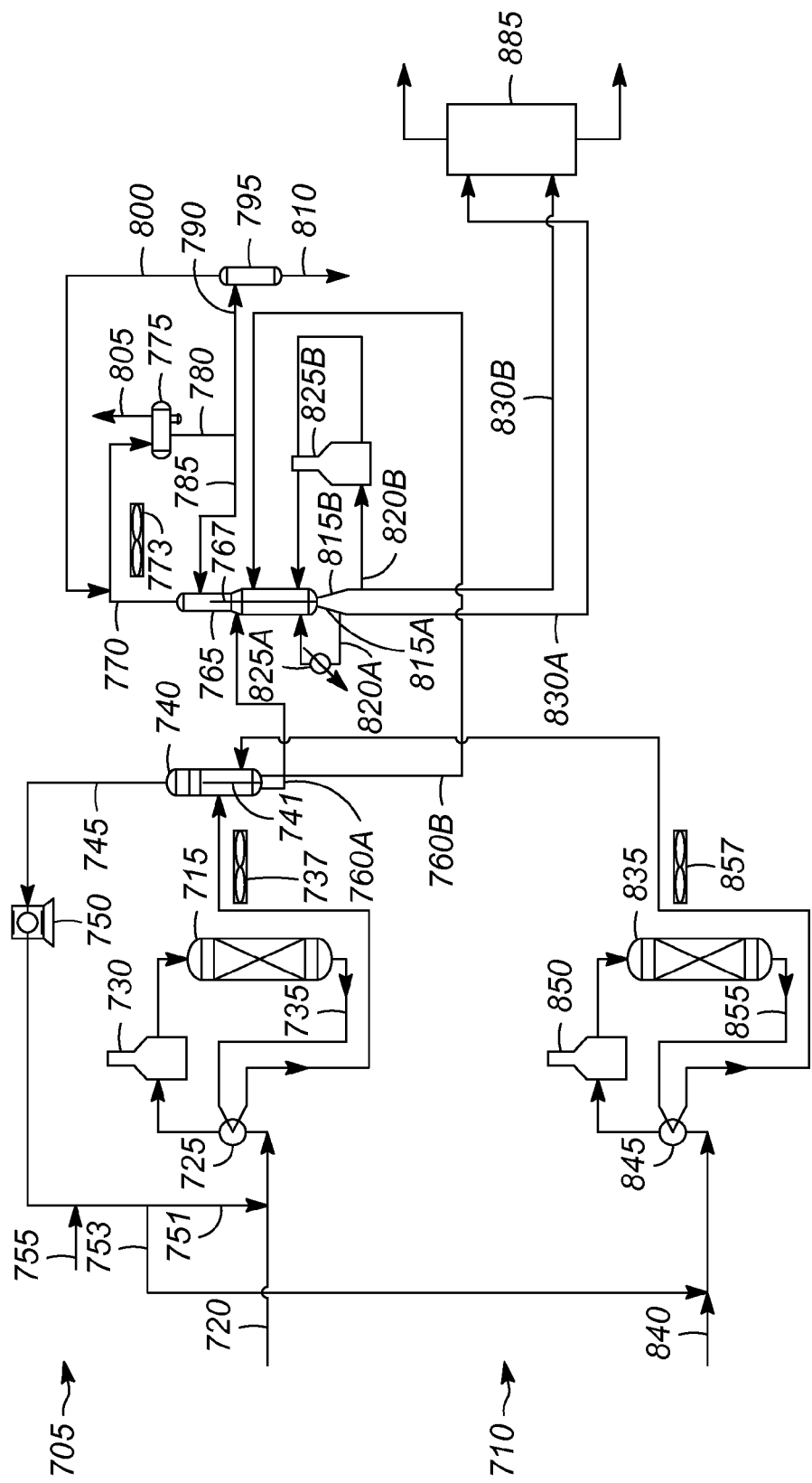
FIG. 4 is another embodiment of a combined isomerization and transalkylation process unit.

FIG. 4 illustrates one embodiment of a combined isomerization and transalkylation unit with a split separator and a split shell fractionation column.

The isomerization unit 705 has an isomerization reactor 715. The feed 720 is pre-heated in a heat exchanger 725 and further heated in a charge heater 730 before entering the isomerization reactor 715. The effluent 735 from the isomerization reactor 715 is sent to the heat exchanger 725, and the condenser 737.

The transalkylation unit 710 has a transalkylation reactor 835. The feed 840 is pre-heated in a heat exchanger 845 and further heated in a charge heater 850 before entering the transalkylation reactor 835. The effluent 855 from the transalkylation reactor 835 is sent to the heat exchanger 845, and the condenser 857.

The separator 740 has a baffle 741 which divides the separator into two sides.

The effluent 735 from the isomerization reactor 715 is sent to one side of the separator 740, while the effluent 855 from the transalkylation reactor 835 is sent to the other side of the separator 740. The baffle 741 extends above the liquid level in the separator and keeps the liquid from the two sides separated.

The overhead 745 from the separator 740 is sent to a recycle gas compressor 750. A portion 751 is recycled back to the isomerization reactor 715, and a portion 753 is recycled back to the transalkylation reactor 835. The recycle can be split using flow control valves. Make-up hydrogen 755 is added to the compressed overhead 745 as needed.

The fractionation column 765 is a split shell fractionation column divided by baffle 767. The liquid 760A from the isomerization side of separator 740 is sent to one side of the column, and the liquid 760B from the transalkylation side of separator 740 is sent to the other side of the column. The baffle extends above the level of both liquid feed inlets.

The overhead 770 is sent to the condenser 773, and the overhead receiver 775. The liquid 780 from the overhead receiver 775 is divided into a reflux stream 785 that is sent back to the split shell fractionation column 765 and a net overhead stream 790 that is sent to a stripper column 795. The overhead 800 from the stripper column 795 is combined with the vapor 770 from the column 765 and recycled back to the condenser 773 and overhead receiver 775. Overhead vapor 805 is removed from overhead receiver 775 to maintain column pressure control. The bottoms 810 from the stripper column 795 is sent to a benzene column or to an aromatic extraction unit (not shown).

Because the baffle 767 extends to the bottom of the split shell fractionation column 765, the liquid bottoms from the isomerization side and the transalkylation side remain separated. The bottoms 815A from the isomerization side of the split shell fractionation column 765 is divided into stream 820A, which is sent to the reboiler 825A and back to the isomerization side of the split shell fractionation column 765, and stream 830A, which is sent to a xylene column 885. Stream 830A is the upper feed for the xylene column 885 because of its low A9+ content.

The bottoms 815B from the transalkylation side of the split shell fractionation column 765 is divided into stream 820B, which is sent to the reboiler 825B and back to the transalkylation side of the split shell fractionation column 765, and stream 830B, which is sent to the xylene column 885. Stream 830B is the lower feed for the xylene column 885 because of its higher A9+ content.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A combined xylene isomerization and transalkylation process comprising:
   isomerizing a feed stream in an isomerization reactor under isomerization conditions to produce an isomerization product;
   transalkylating a feed stream in a transalkylation reactor under transalkylating conditions to produce a transalkylation product;
   providing a split separator having a baffle separating the separator into two sides, the separator having an isomerization inlet on the isomerization side of the baffle and a transalkylation inlet on the transalkylation side of the baffle, the baffle extending from a bottom of the separator to a location above a highest inlet;
   introducing the isomerization product into the isomerization side of the separator through the isomerization inlet;
   introducing the transalkylation product into the transalkylation side of the separator through the transalkylation inlet;
   separating the isomerization product in the isomerization side of the separator to produce a separator isomerization bottoms stream;
   separating the transalkylation product in the transalkylation side of the separator to produce a separator transalkylation bottoms stream; and
   fractionating the separator isomerization bottoms stream and the separator transalkylation bottoms stream in a fractionation column to produce a fractionation column bottoms stream.

2. The process of claim 1 further comprising fractionating the fractionation column bottoms stream in a xylene column.

3. The process of claim 1 further comprising recycling an overhead stream from the separator to the isomerization reactor, or the transalkylation reactor, or both.

4. The process of claim 1 further comprising fractionating an overhead stream from the fractionation column.

* * * * *